United States Patent [19]

Boger

[11] Patent Number: 4,815,660

[45] Date of Patent: Mar. 28, 1989

[54] METHOD AND APPARATUS FOR SPRAYING HOT MELT ADHESIVE ELONGATED FIBERS IN SPIRAL PATTERNS BY TWO OR MORE SIDE-BY-SIDE SPRAY DEVICES

[75] Inventor: Bentley J. Boger, Atlanta, Ga.

[73] Assignee: Nordson Corporation, Amherst, Ohio

[21] Appl. No.: 62,702

[22] Filed: Jun. 16, 1987

[51] Int. Cl.$^4$ .......................... B05D 5/10; B05C 5/04; B05B 7/10; B05B 1/34

[52] U.S. Cl. ........................................ 239/8; 118/302; 156/578; 239/11; 239/298; 239/418; 264/103; 427/286

[58] Field of Search ................... 118/302; 264/103, 12; 239/8, 11, 298, 418; 156/578; 427/286

[56] References Cited

U.S. PATENT DOCUMENTS

| | | | |
|---|---|---|---|
| 721,900 | 3/1903 | Lassoe et al. ............................ 425/7 |
| 2,626,424 | 1/1953 | Hawthorne, Jr. ....................... 425/7 |
| 3,053,461 | 9/1962 | Inglis ..................................... 239/411 |
| 3,096,225 | 7/1963 | Carr et al. ......................... 427/426 X |
| 3,152,923 | 10/1964 | Marshall et al. ........................ 118/2 |
| 3,690,518 | 9/1972 | Baker et al. .......................... 222/504 |
| 3,764,069 | 10/1973 | Runstadler, Jr. et al. ............... 239/8 |
| 3,787,265 | 1/1974 | McGinnis et al. ............. 264/103 X |
| 3,825,379 | 7/1974 | Lohkamp et al. .................... 425/72 |
| 3,841,567 | 10/1974 | Drozek et al. ...................... 239/570 |
| 4,031,854 | 6/1977 | Sprague, Jr. ..................... 118/302 X |
| 4,128,667 | 12/1978 | Timson . | |
| 4,159,199 | 6/1979 | Levecque et al. ....................... 425/7 |
| 4,185,981 | 1/1980 | Ohsato et al. ..................... 264/12 X |
| 4,211,736 | 7/1980 | Bradt ................................ 264/103 X |
| 4,291,157 | 8/1980 | Binoche .............................. 239/296 |
| 4,411,389 | 10/1983 | Harrison ........................... 239/427.5 |

FOREIGN PATENT DOCUMENTS

| | | | |
|---|---|---|---|
| 8534594 | 2/1986 | Fed. Rep. of Germany . | |
| 1109198 | 8/1984 | U.S.S.R. ............................. 239/290 |
| 1240465 | 6/1986 | U.S.S.R. ............................. 239/290 |

Primary Examiner—Philip Anderson
Attorney, Agent, or Firm—Wood, Herron & Evans

[57] ABSTRACT

An apparatus for spraying heated hot melt adhesive in a relatively wide spray pattern comprises a manifold and at least two spray guns mounted side-by-side to the manifold. Each spray gun includes a nozzle having an adhesive discharge passageway which ejects a bead of hot melt adhesive, and a plurality of air jet bores which direct jets of pressurized air to the outer periphery of the adhesive bead to attenuate the bead forming elongated adhesive fibers and to impact a rotational motion to the fibers forming a spiral spray pattern. The air jet bores in the nozzle of one spray gun are angled with respect to the adhesive discharge passageway therein so that the adhesive fibers are rotated in one of a clockwise or counterclockwise direction, whereas the air jet bores in the nozzle of an adjacent spray gun are angled to rotate the adhesive fibers in the other of a clockwise or counterclockwise direction so that adjacent spiral spray patterns are counter-rotating to avoid the formation of eddies or turbulence therebetween.

8 Claims, 1 Drawing Sheet

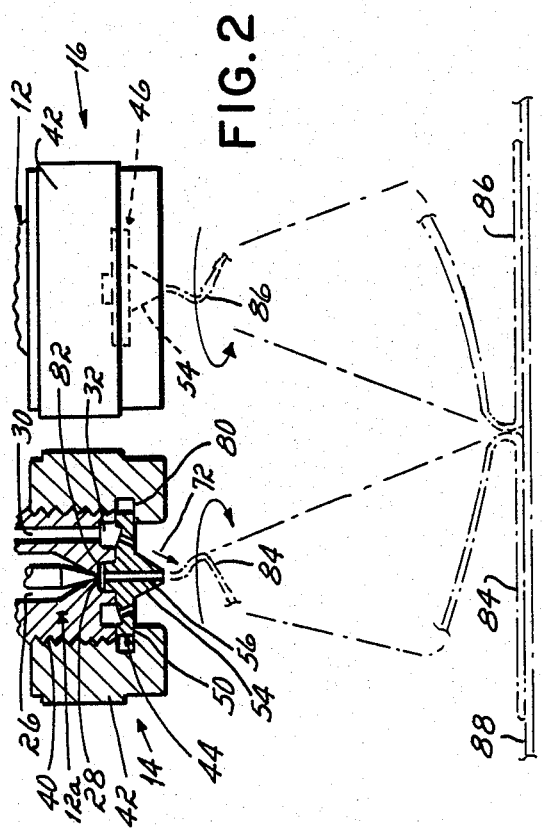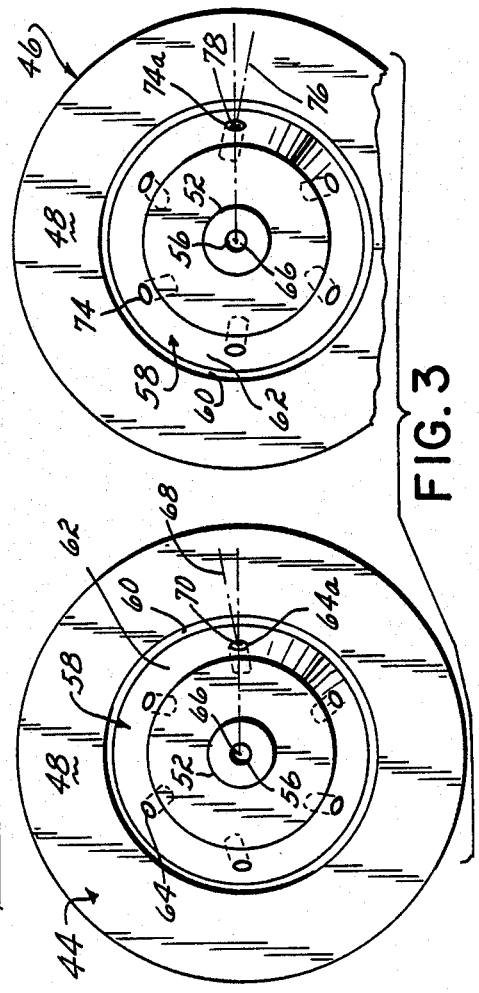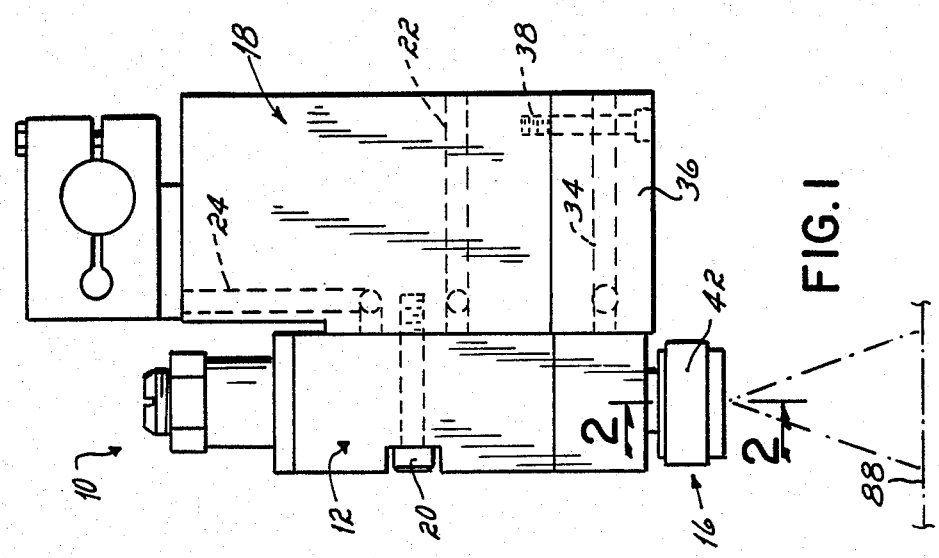

METHOD AND APPARATUS FOR SPRAYING HOT MELT ADHESIVE ELONGATED FIBERS IN SPIRAL PATTERNS BY TWO OR MORE SIDE-BY-SIDE SPRAY DEVICES

FIELD OF THE INVENTION

This invention relates to an adhesive spray apparatus, and, more particularly, to an adhesive spray apparatus having a number of spray guns positioned side-by-side above a substrate, each of which spray elongated fibers of hot melt adhesive in spiral spray patterns which are controlled so that adjacent spray patterns do not interfere with one another.

BACKGROUND OF THE INVENTION

Hot melt thermoplastic adhesives have been widely used in industry for adhering many types of products, and are particularly useful in applications where quick setting time is advantageous. One application for hot melt adhesive which has been of considerable interest in recent years is the bonding of non-woven fibrous material to a polyurethane substrate in articles such as disposable diapers, incontinence pads and similar articles.

One aspect of forming an appropriate bond between the non-woven layer and polyurethane substrate of a disposable diaper, for example, is to avoid loss of adhesive in the valleys or gaps formed in the irregular surface of the chopped fibrous or fluff-type material which forms the non-woven layer. If the adhesive is discharged onto the non-woven layer in droplet form, for example, a portion of the droplets can fall between the gaps in the surface of the fibrous, non-woven material. As a result, additional quantities of adhesive are required to obtain the desired bond strength between the polyurethane substrate and non-woven material.

This problem has been overcome in the prior art by forming hot melt thermoplastic adhesives in elongated, thin beads or fibers which are deposited atop the non-woven material and span the gaps in its irregular surface. Elongated beads or fibers of adhesive have been produced in prior art spray devices which include a nozzle formed with an adhesive discharge opening and one or more air jet orifices through which a jet of air is ejected. A bead of adhesive is ejected from the adhesive discharge opening in the nozzle which is then impinged by the air jets to attenuate or stretch the adhesive bead forming a thin fiber for deposition onto the substrate. Examples of spray devices of this type are disclosed in U.S. Pat. Nos. 2,626,424 to Hawthorne, Jr.; 3,152,923 to Marshall et al; and, 4,185,981 to Ohsato et al.

In applications such as the formation of disposable diapers, it is important to carefully control the spray pattern of adhesive fibers deposited onto the non-woven substrate in order to obtain the desired bond strength between the non-woven layer and polyurethane substrates using as little adhesive as possible. Improved control of the spray pattern of adhesive fibers has been obtained in prior art spray devices of the type described above by directing the air jets which impact the adhesive bead discharged from the nozzle substantially tangent to the outer periphery of the adhesive bead. The tangentially directed air jets rotate the elongated fibers of adhesive formed from the adhesive bead ejected from the adhesive discharge opening in the gun nozzle in a relatively tight, compact spiral pattern for application onto the substrate. Structure which produces a spiral spray pattern of adhesive fibers for deposition onto a substrate is disclosed, for example, in the '424 Hawthorne, Jr. patent and '981 Ohsato et al patent mentioned above.

In order to obtain a spray pattern upon a substrate which is wider than that produced by a single gun, while at the same time controlling the location of the pattern or the substrate, two or more spray guns each effective to produce a separate spiral spray pattern are required. To avoid gaps in the adhesive layer applied to the substrate, and/or prevent overlapping of adjacent spray patterns which could result in an unwanted buildup of adhesive, the separate spiral spray patterns from adjacent guns are preferably tangent to one another at or near the surface of the substrate. This has presented a problem in the prior art wherein adjacent rotating spiral spray patterns form eddies or turbulence in the area where they contact one another. This turbulence disrupts the spray pattern near the surface of the substrate and also tends to lift at least some of the attenuated adhesive fibers back upstream toward the spray guns where they adhere to the equipment. It also creates gaps in the spray pattern.

SUMMARY OF THE INVENTION

It is therefore among the objectives of this invention to provide an adhesive spray apparatus which is capable of dispensing a relatively wide spray pattern onto a substrate from a number of individual spray guns while avoiding interference between the spray patterns from adjacent guns.

This objective is accomplished in an adhesive spray apparatus in which two or more spray devices are positioned side-by-side above a substrate and produce counter-rotating spiral spray patterns of hot melt adhesive fibers, i.e., alternating clockwise and counterclockwise rotating spray patterns. The spray patterns from adjacent guns are tangent to one another at or near the surface of the substrate to be coated, but avoid interference with one another upon impact so as to eliminate the creation of eddies or turbulence which could disrupt the spray pattern on the substrate.

In the presently preferred embodiment, the spray apparatus comprises two or more adhesive spray guns mounted side-by-side to a manifold having an adhesive supply passageway connected to a source of hot melt adhesive and an air supply passageway connected to a source of pressurized air. Each of the spray guns is formed with a nozzle having an adhesive discharge passageway communicating with the adhesive supply passageway of the manifold. The nozzle is also provided with a plurality of air jets each communicating with the air supply passageway of the manifold. A bead of hot melt adhesive is ejected from each nozzle which is impacted at its outer periphery by jets of air from the air discharge orifices of the nozzle to attenuate the adhesive bead forming elongated adhesive fibers, and to impart a rotation or twisting motion to the elongated fibers forming a spiral spray pattern.

The air discharge orifices in the nozzle of one spray gun are oriented to impart a clockwise rotation to the elongated adhesive fibers formed thereat, and the air discharge orifices in the nozzle of an adjacent spray gun are oriented to impart a counterclockwise motion to the elongated fibers formed at such adjacent nozzle. The counter-rotating spiral spray patterns from the two nozzles preferably contact one another at or near the surface of the target substrate, but do not deflect or interfere with each other and therefore avoid the formation of eddies or turbulence which can disrupt the spray pattern.

In a presently preferred embodiment, the nozzle of each of the spray guns is provided with a nozzle attachment in the form of a one-piece annular plate which is mounted by a cap to the nozzle. The nozzle attachment or plate is formed with a throughbore adapted to connect to the adhesive discharge opening in the nozzle, and a plurality of spaced air jet bores which communicate with the air discharge opening in the nozzle. An adhesive bead is ejected from the throughbore in the plate which is impacted by air jets from the spaced air jet bores. The air jets are directed tangentially to the bead to both stretch the bead forming hot melt adhesive fibers, and to impart a spiral motion to the fibers so that they are deposited in a controlled spray pattern upon the substrate.

In the nozzle attachment for one spray gun, the spaced air jet bores are formed at an angle relative to the outer periphery of the throughbore therein and the adhesive bead ejected from the throughbore. The longitudinal axis of each air jet bore is angled approximately 10° with respect to a vertical plane which passes through the longitudinal axis of the throughbore in the plate and the center of each such air jet bore at the top surface of the plate. As a result, the jets of pressurized air ejected from the spaced air jet bores impact the adhesive bead discharged from the throughbore of the plate at its outer periphery so as to impart a rotational movement to the bead in one of a clockwise or counterclockwise direction.

The nozzle attachment for an adjacent spray gun is formed in the same manner except the angle of the air jet bores is formed 10° in the opposite direction from that of the air jet bores in the first nozzle attachment. In other words, if two adjacent nozzle attachments were placed one on top of the other so that their throughbores align, and the center of each bore at the top surface of nozzle attachments align, the angle between the longitudinal axis of the air jet bores of one nozzle attachment would be spaced 20° from the longitudinal axis of the air jet bores in the adjacent nozzle attachment. The air jets from the air jet bores of such adjacent nozzle attachment therefore impact the outer periphery of the adhesive bead in the opposite direction to impart a rotation to such adhesive bead in the other of a clockwise or counterclockwise direction.

DETAILED DESCRIPTION OF THE DRAWINGS

The structure, operation and advantages of the presently preferred embodiment of this invention will become further apparent upon consideration of the following description taken in conjunction with the accompanying drawings, wherein:

FIG. 1 is an elevational view of one spray gun and the manifold to which it is mounted;

FIG. 2 is a partial side view taken generally along line 2—2 of FIG. 1 showing the lower portion of two spray guns in the apparatus of this invention mounted side-by-side;

FIG. 3 is a top plan view of the nozzle attachments shown in FIG. 2.

DETAILED DESCRIPTION OF THE INVENTION

Referring now to FIGS. 1 and 2, an adhesive spray apparatus 10 is illustrated which comprises a pair of adhesive spray guns 12, 12a having nozzles 14 and 16 connected at one end. The spray guns 12, 12a are mounted to an adhesive manifold 18 by screws 20. The adhesive manifold 18 is formed with an adhesive supply passageway 22 and an air supply passageway 24 which communicate with each of the spray guns 12, 12a. The spray guns 12, 12a are operated by pressurized air from the air supply passageway 24 to discharge hot melt adhesive provided by the adhesive supply passageway 22 through the nozzles 14 and 16. The detailed structure of spray guns 12, 12a and adhesive manifold 18 are substantially identical to that illustrated in U.S. Pat. No. 3,690,518, owned by the assignee of this invention, and form no part of this invention per se. Reference to such '518 patent should be made for a detailed discussion of the operation of spray guns 12, 12a and adhesive manifold 18.

The nozzles 14, 16 of each spray gun 12, 12a are formed with an adhesive passageway 26 which communicates with the adhesive supply passageway 22 and terminates at an adhesive discharge opening 28. An air delivery passageway 30 is also formed in each nozzle 14, 16 which terminates at an annular chamber 32 in the base of the nozzle. The air delivery passageway 30 is supplied with pressurized air through an air inlet line 34 formed in an air manifold 36 connected to the adhesive manifold 18 by screws 38. In the presently preferred embodiment, the nozzle 14, 16 of each spray gun 12, 12a is formed with a reduced diameter portion having external threads 40 which mate with internal threads formed in a cap 42. As described below, one cap 42 mounts a first nozzle attachment 44 to spray nozzle 14 and another cap 42 mounts a second nozzle attachment 46 to the spray nozzle 16.

Referring now to the bottom of FIGS. 2 and 3, each of the nozzle attachments 44, 46 are shown in detail. The structure of such nozzle attachments 44, 46 is discussed in detail in co-pending patent application Ser. No. 041,712, filed Apr. 23, 1987 and now U.S. Pat. No. 4,785,996 and owned by the same assignee as this invention, which is incorporated by reference in its entirety herein. For purposes of the present discussion, the nozzle attachments 44, 46 are described briefly and structure common to both attachments 44, 46 is given the same reference numbers.

The nozzle attachment 44 comprises an annular plate having one side formed with a first or upper surface 48 and an opposite side formed with a second or lower surface 50 spaced from the upper surface 48. A boss 52 extends outwardly from the upper surface 48 and a nozzle tip 54 extends outwardly from the lower surface 50 in alignment with the boss 52. A throughbore 56 is formed in the nozzle attachment between the boss 52 and nozzle tip 54.

An annular V-shaped groove 58 is formed in the nozzle attachment which extends inwardly from its upper surface 48 toward the lower surface 50. The annular groove 58 defines a pair of sidewalls 60, 62 which are substantially perpendicular to one another. In the presently preferred embodiment, the sidewall 62 is formed at approximately a 30° angle with respect to the planar upper surface 48 of the nozzle attachment. As best illustrated in FIG. 3, six air jet bores 64 are formed in a nozzle attachment of spray gun each having an inlet at the annular groove 58 and an outlet at the lower surface 50. Preferably, the air jet bores 64 extend at an angle of approximately 30° with respect to the longitudinal axis of the throughbore 56. As discussed in detail in the co-pending application Ser. No. 041,712, mentioned above, now U.S. Pat. No. 4,785,996, the annular groove 58 facilitates drilling of the air jet bores 64 to ensure they are accurately positioned.

The longitudinal axis of each of the air jet bores 64 of first nozzle attachment 44 is angled approximately 10° in a counterclockwise direction as viewed in FIG. 3 with respect to a vertical plane passing through the longitudinal axis 66 of throughbore 56 and the center of the inlet of each such air jet bore 64 at the annular groove 58. For example, the longitudinal axis 68 of air jet bore 64a is angled approximately 10° relative to a vertical plane passing through the longitudinal axis 66 of throughbore 56 and the centerpoint 70 of the inlet of bore 64a at the annular groove 58 in nozzle attachment 44. As a result, a jet of pressurized air 72 ejected from the outlet of air jet bore 64a is directed substantially tangent to the outer periphery of the throughbore 56 and the adhesive bead ejected therefrom, as described in more detail below.

The second nozzle attachment 46 mounted to the spray gun 14 is identical to first nozzle attachment 44 except for the angular orientation of the six air jet bores 74 formed therein which correspond to the air jet bores 64 of the first nozzle attachment 44. Air jet bores 74 are angled at approximately 10° in a clockwise direction as viewed in FIG. 3 with respect to a vertical plane passing through the longitudinal axis of the throughbore 56 and the center of the inlet of each such bore 74 at the annular groove 58. For example, the longitudinal axis 76 of air jet bore 74a is angled approximately 10° in a clockwise direction relative to a vertical plane passing through the longitudinal axis 66 of throughbore 56 and the centerpoint 78 of the inlet of air jet bore 74a at the annular groove 58 in nozzle attachment 46.

The angular orientation of the air jet bores 74 of second nozzle attachment 46 relative to the throughbore 56 is essentially the mirror image of the position of air jet bores 64 of the first nozzle attachment 44. In other words, if the first nozzle attachment 44 was placed atop the second nozzle attachment 46 such that their throughbores 56 align, and the centerpoint 70 of air jet bore 64a aligned with the centerpoint 78 of air jet bore 74a, the longitudinal axis of each air jet bores 64 would be spaced 20° from the longitudinal axis of each corresponding air jet bore 74.

Both the first and second nozzle attachments 44, 46 rest upon an annular seat 80 formed in the caps 42. The cap 42 is threaded onto the lowermost end of nozzles 14, 16 so that the boss 52 on the upper surface 48 of nozzle attachments 44, 46 extends within a seat or recess 82 formed in the base of nozzles 14 and 16 at the adhesive discharge opening 28 of adhesive passageway 26.

The operation of the spray apparatus 10 of this invention is as follows. Heated hot melt adhesive is introduced through the adhesive supply passageway 22 into each of the spray guns 12, 12a where it flows through the adhesive passageway 26 to the adhesive discharge opening 28 in the nozzles 14 and 16. Each of the spray guns 12, 12a is air-operated to open and close the flow of adhesive through the adhesive discharge opening 28. From the nozzles 14 and 16, the heated hot melt adhesive is transferred into the throughbore 56 of each nozzle attachment 44, 46 and then discharged through the nozzle tips 54 thereof to form first and second adhesive beads 84, 86, respectively. At the same time the adhesive beads 84, 86 are formed and ejected from the nozzle attachments 44, 46, pressurized air is directed through the air supply passageway 34, through the air delivery passageway 30 in nozzles 14 and 16 and then to the annular chamber 32 in the nozzles 14, 16 of each spray gun 12, 12a, which communicate with the air jet bores 64 and 74, respectively.

As best shown in FIG. 3, the air jet bores 64 of first nozzle attachment 44 are angled relative to the longitudinal axis of the throughbore 56 so that the jets of air flowing therethrough impact the first adhesive bead 84 substantially tangent to its outer periphery at a point spaced below the nozzle tip 54. The air ejected from the air jet bore 64 performs two functions. First, the jets of air attenuate or stretch the first adhesive bead 84 forming elongated strands or fibers of hot melt adhesive for deposit onto a substrate 88. Additionally, the tangential impact of the air jet streams from the six bores 64 imparts a clockwise rotation or twisting motion to the elongated fibers forming them in a compact spiral pattern for deposition onto the substrate 88.

The same spiral spray pattern of adhesive fibers is obtained from the nozzle 16 of spray gun 14 in the same manner as in the nozzle 14, except the direction of rotation of the elongated adhesive fibers is counterclockwise in the illustration of FIG. 3. In second nozzle attachment 46, the air jet bores 74 are angled relative to the longitudinal axis of the throughbore 56 so that the jets of air flowing therethrough impact the outer periphery of the second adhesive bead 86 in the opposite direction such that the elongated fibers of hot melt adhesive are rotated or twisted in the counterclockwise direction instead of a clockwise direction.

The counter-rotating spiral spray patterns from spray nozzles 14 and 16 contact one another at or near the top surface of the substrate 88. Because the two spray patterns are rotating in opposite directions, they do not interfere with one another upon impact and thus produce little or no turbulence or eddies which can disrupt the spray pattern, produce an uneven application of adhesive onto the substrate and/or force some of the elongated fibers upstream toward the spray guns 12, 12a.

While the invention has been described with reference to a preferred embodiment, it will be understood by those skilled in the art that various changes may be made and equivalents may be substituted for elements thereof without departing from the scope of this invention. In addition, many modifications may be made to adapt a particular situation or material to the teachings of the invention without departing from the essential scope thereof.

For example, only two spray guns 12, 12a were illustrated in the Figs. It should be understood that the spray apparatus 10 could be formed with essentially any number of spray guns 12, 12a mounted side-by-side to a manifold 18 depending upon the width of the spray pattern desired. In such instance, the direction of rotation of adjacent spiral spray patterns would be opposite so as to avoid interference therebetween in accordance with the teachings of this invention.

Therefore, it is intended that the invention not be limited to the particular embodiment disclosed as the best mode contemplated for carrying out this invention, but that the invention will include all embodiments falling within the scope of the appended claims.

I claim:

1. A method of spraying heated hot melt adhesive comprising:
   ejecting a first heated hot melt adhesive bead from the adhesive discharge passageway of a first dispensing device;
   impacting the outer periphery of said first adhesive bead from said first dispensing device with jets of air ejected from air discharge passageways in said first dispensing device to form said first adhesive bead into elongated adhesive fibers and to impart a clockwise twisting motion to said elongated adhesive fibers forming a first spiral spray pattern;
   ejecting a second heated hot melt adhesive bead from the adhesive discharge passageway of a second dispensing device positioned beside said first dispensing device;
   impacting the outer periphery of said second adhesive bead from said second dispensing device with jets of air ejected from air discharge passageways in said second dispensing device to form said second adhesive bead into elongated adhesive fibers and to impart a counterclockwise twisting motion to said elongated adhesive fibers forming a second spiral spray pattern.

2. The method of claim 1 further comprising the step of positioning said first and second dispensing devices so that said first and second spray patterns therefrom overlap to form a combined spray pattern having approximately twice the width of one of said first and second spray patterns.

3. A method of spraying molten thermoplastic material comprising:
   ejecting a first heated hot melt adhesive bead from the adhesive discharge passageway of a first dispensing device;
   impacting the outer periphery of said first adhesive bead from said first dispensing device with jets of air ejected from air discharge passageways in said first dispensing device to form said first adhesive bead into elongated adhesive fibers and to impart a clockwise twisting motion to said elongated adhesive fibers forming a first spiral spray pattern;
   ejecting a second heated hot melt adhesive bead from the adhesive discharge passageway of a second dispensing device positioned beside said first dispensing device;
   impacting the outer periphery of said second adhesive bead from said second dispensing device with jets of air ejected from air discharge passageways in said second dispensing device to form said second adhesive bead into elongated adhesive fibers and to impart a counterclockwise twisting motion to said elongated adhesive fibers forming a second spiral spray pattern.

4. Apparatus for spraying hot melt adhesive comprising:
   a manifold formed with an adhesive supply passageway connected to a source of heated hot melt adhesive, and formed with an air supply passageway connected to a source of pressurized air;
   first and second dispensing devices mounted side-by-side to said manifold, said first and second dispensing devices each having a spray nozzle formed with an adhesive discharge passageway communicating with said adhesive supply passageway, said adhesive discharge passageways of said first and second dispensing devices ejecting first and second beads of heated hot melt adhesive, respectively, each having an outer periphery;
   said spray nozzle of said first dispensing device having a plurality of first air discharge passageways communicating with said air supply passageway, said first air discharge passageways being formed at an angle with respect to said adhesive discharge passageway of said first dispensing device to direct pressurized air substantially tangent to said outer periphery of said first adhesive bead ejected from said adhesive discharge passageway of said first dispensing device, the pressurized air from said first air discharge passageways being effective to form said first adhesive bead into elongated adhesive fibers and to impart a twisting motion to said elongated adhesive fibers in one of a clockwise or counterclockwise direction to form a spiral spray pattern of elongated adhesive fibers;
   said spray nozzle of said second dispensing device being formed with a plurality of second air discharge passageways communicating with said air supply passageway, said second air discharge passageways being formed at an angle with respect to said adhesive discharge passageway of said second dispensing device to direct pressurized air substantially tangent to said outer periphery of said second adhesive bead ejected from said adhesive discharge passageway of said second dispensing device, the pressurized air from said second air discharge passageways being effective to form said second adhesive bead into elongated adhesive fibers and to impart a twisting motion to said elongated adhesive fibers in the other of said clockwise and counterclockwise directions to form a spiral spray pattern of elongated adhesive fibers.

5. The apparatus of claim 4 in which each of said first air discharge passageways is formed with an inlet, an outlet and a longitudinal axis extending between the centerpoint of said inlet and outlet, said first air discharge passageways of said first dispensing device being disposed at an angle of approximately 10° relative to a vertical plane passing through the longitudinal axis of said adhesive discharge passageway and said centerpoint of said inlet of each said first air discharge passageways, said angle being such that pressurized air ejected from each said first air discharge passageways contacts said periphery of said first adhesive bead ejected from said adhesive discharge passageway of said first dispensing device to rotate said first adhesive bead in a clockwise direction.

6. The apparatus of claim 4 in which each of said second air discharge passageways is formed with an inlet, an outlet and a longitudinal axis extending between the centerpoint of said inlet and outlet, said second air discharge passageways of said second dispensing device being disposed at an angle of approximately 10° relative to a vertical plane passing through the longitudinal axis of said adhesive discharge passageway and said centerpoint of said inlet of each said second air discharge passageways, said angle being such that pressurized air ejected from each said second air discharge passageways contacts said periphery of said second adhesive bead ejected from said adhesive discharge passageway of said second dispensing device to rotate said second adhesive bead in a counterclockwise direction.

7. Apparatus for spraying heated hot melt adhesive comprising:

means for ejecting a first heated hot melt adhesive bead from the adhesive discharge passageway of a first dispensing device;

means for impacting the outer periphery of said first adhesive bead from said first dispensing device with jets of air ejected from air discharge passageways in said first dispensing device to form said first adhesive bead into elongated adhesive fibers and to impart a clockwise twisting motion to said elongated adhesive fibers forming a first spiral spray pattern;

means for ejecting a second heated hot melt adhesive bead from the adhesive discharge passageway of a second dispensing device positioned beside said first dispensing device; and means for impacting the outer periphery of said second adhesive bead from said second dispensing device with jets of air ejected from air discharge passageways in said second dispensing device to form said second adhesive bead into elongated adhesive fibers and to impart a counterclockwise twisting motion to said elongated adhesive fibers forming a second spiral spray pattern.

8. Apparatus for spraying molten thermoplastic material, comprising:

means for ejecting a first heated hot melt adhesive bead from the adhesive discharge passageway of a first dispensing device;

means for impacting the outer periphery of said first adhesive bead from said first dispensing device with jets of air ejected from air discharge passageways in said first dispensing device to form said first adhesive bead into elongated adhesive fibers and to impart a clockwise twisting motion to said elongated adhesive fibers forming a first spiral spray pattern;

means for ejecting a second heated hot melt adhesive bead from the adhesive discharge passageway of a second dispensing device positioned beside said first dispensing device; and means for impacting the outer periphery of said second adhesive bead from said second dispensing device with jets of air ejected from air discharge passageways in said second dispensing device to form said second adhesive bead into elongated adhesive fibers and to impart a counterclockwise twisting motion to said elongated adhesive fibers forming a second spiral spray pattern.

* * * * *